US011529254B2

(12) United States Patent
Tretheway et al.

(10) Patent No.: US 11,529,254 B2
(45) Date of Patent: Dec. 20, 2022

(54) DRAINABLE OSTOMY APPLIANCE

(71) Applicant: SALTS HEALTHCARE LIMITED, Birmingham (GB)

(72) Inventors: Lee Tretheway, Birmingham (GB); Lee Howard, Birmingham (GB); Iain Powner, Birmingham (GB); Jesus Alfaro, Birmingham (GB)

(73) Assignee: SALTS HEALTHCARE LIMITED, Birmingham (GB)

( * ) Notice: Subject to any disclaimer, the term of this patent is extended or adjusted under 35 U.S.C. 154(b) by 151 days.

(21) Appl. No.: 16/823,087

(22) Filed: Mar. 18, 2020

(65) Prior Publication Data

US 2020/0214875 A1    Jul. 9, 2020

Related U.S. Application Data

(63) Continuation of application No. PCT/GB2018/052689, filed on Sep. 21, 2018.

(30) Foreign Application Priority Data

Sep. 22, 2017    (GB) .................................... 1715390

(51) Int. Cl.
*A61F 5/448* (2006.01)
*A61F 5/445* (2006.01)
*A61F 5/44* (2006.01)

(52) U.S. Cl.
CPC .............. *A61F 5/448* (2013.01); *A61F 5/445* (2013.01); *A61F 2005/4483* (2013.01)

(58) Field of Classification Search
CPC ... A61F 5/448; A61F 2005/4483; A61F 5/445
See application file for complete search history.

(56) References Cited

U.S. PATENT DOCUMENTS 2,520,831 A * 8/1950 Chincholl ............... A61F 5/445
                                                    604/335
3,507,282 A * 4/1970 Burdingjudys ......... A61F 5/445
                                                    604/333
(Continued)

FOREIGN PATENT DOCUMENTS

GB    2414677 A  * 12/2005  ............. A61F 5/445
WO    2003086250 A1   10/2003
WO    2007115574 A1   10/2007

OTHER PUBLICATIONS

International Search Report in related International Application No. PCT/GB2018/052689 dated Mar. 1, 2019 (5 pages).
(Continued)

*Primary Examiner* — Guy K Townsend
(74) *Attorney, Agent, or Firm* — Pillsbury Winthrop Shaw Pittman, LLP

(57) ABSTRACT

A drainable ostomy appliance including: first and second walls connected to each other at or near their peripheries, the first wall having a stoma-receiving opening; a collecting cavity defined between the first and second walls; a connection member connected to the first wall for attaching the appliance to a user or for attaching the appliance to a flange for attaching the appliance to a user; an outlet which extends away from the stoma-receiving opening, the outlet terminating at an opening; and a first stiffening member positioned immediately adjacent the opening on a wall of the outlet facing the user, in use, the first stiffening member extending across the outlet; and a second stiffening member positioned next to the first stiffening member, further away from the outlet than the first stiffening member and on the same wall as the first stiffening member, the second stiffening member also extending across the outlet.

17 Claims, 8 Drawing Sheets

(56) References Cited

U.S. PATENT DOCUMENTS

| | | | | |
|---|---|---|---|---|
| 3,690,320 | A | * | 9/1972 | Riely .................... A61F 5/4407 604/335 |
| 3,825,005 | A | * | 7/1974 | Fenton .................. A61F 5/4407 604/335 |
| 4,233,977 | A | * | 11/1980 | Mattson ................ A61F 5/4407 604/335 |
| 4,403,991 | A | * | 9/1983 | Hill ........................ A61F 5/443 604/338 |
| 4,460,359 | A | * | 7/1984 | Fenton .................. A61F 5/4407 604/277 |
| 4,465,486 | A | * | 8/1984 | Hill ........................ A61F 5/443 24/30.5 R |
| 4,755,177 | A | * | 7/1988 | Hill ........................ A61F 5/443 604/339 |
| 4,983,172 | A | * | 1/1991 | Steer .................. B65D 33/1675 604/277 |
| 4,988,343 | A | * | 1/1991 | Ballan .................... A61F 5/4407 383/66 |
| 5,968,023 | A | * | 10/1999 | Olsen .................... A61F 5/4407 24/30.5 R |
| 6,336,918 | B1 | * | 1/2002 | Olsen .................... A61F 5/4407 604/355 |
| 6,419,664 | B1 | * | 7/2002 | von Bulow ........... A61F 5/4407 604/327 |
| 6,544,241 | B2 | * | 4/2003 | Morton .................. A61F 5/4407 604/317 |
| 6,589,221 | B1 | * | 7/2003 | Olsen .................... A61F 5/4407 604/332 |
| 6,887,222 | B2 | * | 5/2005 | Mandzij ................. A61F 5/4407 604/277 |
| 7,223,260 | B2 | * | 5/2007 | Hansen .................. A61F 5/4407 604/338 |
| 7,306,581 | B2 | * | 12/2007 | Falconer ............... A61F 5/4407 604/339 |
| 7,468,056 | B2 | * | 12/2008 | Burt ....................... A61F 5/4405 604/326 |
| D618,791 | S | * | 6/2010 | Schena ........................ D24/118 |
| 7,879,015 | B2 | * | 2/2011 | Villefrance ............. A61F 5/445 604/338 |
| 7,947,025 | B2 | * | 5/2011 | Buglino .................. A61F 5/445 604/335 |
| 8,206,364 | B2 | * | 6/2012 | Schertiger ............. A61F 5/4407 604/327 |
| 8,449,511 | B2 | * | 5/2013 | Andersen ................ A61F 5/443 604/326 |
| 8,500,707 | B2 | * | 8/2013 | Murray .................... A61F 5/445 383/88 |
| 8,672,907 | B2 | * | 3/2014 | Friske .................... A61F 5/4407 604/335 |
| 8,821,463 | B2 | * | 9/2014 | Grum-Schwensen ....................... A61F 5/443 604/332 |
| 9,011,395 | B2 | * | 4/2015 | Friske .................... A61F 5/4407 604/332 |
| 9,066,807 | B2 | * | 6/2015 | Tsai ....................... A61F 5/4407 |
| 9,629,744 | B2 | * | 4/2017 | Villefrance ........... A61F 5/4405 |
| 9,668,910 | B2 | * | 6/2017 | Murray .................. A61F 5/4407 |
| 9,949,864 | B2 | * | 4/2018 | Ben-Arie ............... A61F 5/4407 |
| 9,956,110 | B2 | * | 5/2018 | Ben-Arie ................ A61F 5/445 |
| 10,478,330 | B2 | * | 11/2019 | Wiltshire ................. A61F 5/445 |
| 10,660,785 | B2 | * | 5/2020 | Kaufman ................ A61F 5/442 |
| 10,813,786 | B2 | * | 10/2020 | Lysgaard ............... A61F 5/4404 |
| 11,039,950 | B2 | * | 6/2021 | Jones, Jr. ............... A61F 5/442 |
| 2002/0010444 | A1 | * | 1/2002 | Wiltshire ................ A61F 5/445 604/335 |
| 2003/0028160 | A1 | * | 2/2003 | Leise, Jr. ................ A61F 5/445 604/334 |
| 2003/0073962 | A1 | * | 4/2003 | Olsen ...................... A61F 5/445 604/327 |
| 2003/0153882 | A1 | * | 8/2003 | Mandzij ................. A61F 5/4407 604/339 |
| 2003/0167042 | A1 | * | 9/2003 | Poulsen ................. A61F 5/4407 604/327 |
| 2004/0049837 | A1 | * | 3/2004 | Falconer ............... A61F 5/4407 383/88 |
| 2004/0068243 | A1 | * | 4/2004 | Hansen ................. A61F 5/4407 604/327 |
| 2005/0131360 | A1 | * | 6/2005 | Villefrance ............. A61F 5/445 604/332 |
| 2005/0159717 | A1 | * | 7/2005 | Holtermann .......... A61F 5/4407 604/332 |
| 2005/0283126 | A1 | * | 12/2005 | Schena .................. A61F 5/442 604/335 |
| 2006/0111682 | A1 | * | 5/2006 | Schena .................. A61F 5/442 604/334 |
| 2007/0265588 | A1 | * | 11/2007 | Pedersen ............... A61F 5/4407 604/340 |
| 2008/0033379 | A1 | * | 2/2008 | Pedersen ............... A61F 5/4407 604/335 |
| 2008/0097360 | A1 | * | 4/2008 | Andersen ............... A61F 5/4407 604/332 |
| 2009/0043271 | A1 | * | 2/2009 | Winther ................. A61F 5/4407 604/332 |
| 2009/0082743 | A1 | * | 3/2009 | Buglino ................. A61F 5/4405 604/335 |
| 2009/0143755 | A1 | * | 6/2009 | Schertiger ............... A61F 5/445 29/428 |
| 2009/0192479 | A1 | * | 7/2009 | Schertiger ............. A61F 5/4407 604/332 |
| 2010/0174254 | A1 | * | 7/2010 | Tsai ....................... A61F 5/4407 604/332 |
| 2011/0028923 | A1 | * | 2/2011 | Murray .................. A61F 5/4405 604/332 |
| 2011/0028924 | A1 | * | 2/2011 | Murray .................. A61F 5/4407 604/332 |
| 2011/0144601 | A1 | * | 6/2011 | Villefrance ........... A61F 5/4405 604/340 |
| 2012/0022477 | A1 | * | 1/2012 | Grum-Schwensen ....................... A61F 5/443 604/332 |
| 2017/0209297 | A1 | * | 7/2017 | Lysgaard ............... A61F 5/4404 |
| 2018/0333290 | A1 | * | 11/2018 | Jones ...................... A61F 5/441 |
| 2019/0029868 | A1 | * | 1/2019 | Grum-Schwensen ....................... A61F 5/4407 |
| 2019/0328572 | A1 | * | 10/2019 | Weinberg ................ A61F 5/445 |
| 2020/0214872 | A1 | * | 7/2020 | Tretheway ............. A61F 5/443 |
| 2020/0214873 | A1 | * | 7/2020 | Tretheway ............ A61F 5/4407 |
| 2020/0214875 | A1 | * | 7/2020 | Tretheway ............. A61F 5/445 |
| 2020/0229962 | A1 | * | 7/2020 | Torstensen ........... A61F 5/4407 |
| 2020/0246173 | A1 | * | 8/2020 | Schertiger .............. A61F 5/443 |
| 2020/0281761 | A1 | * | 9/2020 | Tretheway ............ A61F 5/4404 |

OTHER PUBLICATIONS

Written Opinion in related International Application No. PCT/GB2018/052689 dated Mar. 28, 2019 (6 pages).

* cited by examiner

DRAINABLE OSTOMY APPLIANCE

RELATED APPLICATIONS

This application is a continuation of PCT/GB2018/052689 filed on Sep. 21, 2018, which claims priority to GB 1715390.9 filed on Sep. 22, 2017. The entire contents of each aforelisted patent filing are hereby fully incorporated by reference herein for all purposes.

DESCRIPTION OF INVENTION

The invention relates to ostomy appliances. In particular, but not exclusively, the invention relates to drainable or ileostomy appliances.

It is known to provide drainable ostomy appliances with means to assist in opening and closing an opening thereof to permit the contents of the device to be emptied. However, openings can become stuck in a closed condition, in use. This makes it difficult for a user to manipulate the opening. In particular, if stiffening members are used at or near the exit of the opening and the opening becomes stuck in a closed condition, users may find it difficult to open the opening by applying finger pressure alone to the ends of the stiffening members. This is because the stiffening members present will all tend to bow in the same direction, resulting in the opening remaining closed. It can also become difficult to clean the opening of such an ostomy appliance effectively. Ineffective cleaning can result in the leakage of waste from the device, which is clearly undesirable.

The present invention seeks to address these problems.

According to a first aspect of the invention we provide a drainable ostomy appliance including:

- first and second walls connected to each other at or near their peripheries, the first wall having a stoma-receiving opening;
- a collecting cavity defined between the first and second walls;
- a connection member connected to the first wall for attaching the appliance to a user or for attaching the appliance to a flange for attaching the appliance to a user;
- an outlet which extends away from the stoma-receiving opening, the outlet terminating at an opening; and
- a first stiffening member positioned immediately adjacent the opening on a wall of the outlet which faces the user, in use, the first stiffening member extending across the outlet; and
- a second stiffening member positioned next to the first stiffening member, further away from the outlet than the first stiffening member and on the same wall as the first stiffening member, the second stiffening member also extending across the outlet.

Further features of the various aspects of the invention are set out in the appended claims.

Embodiments of the invention will now be described by way of example only with reference to the accompanying drawings, of which:

Figure 1:
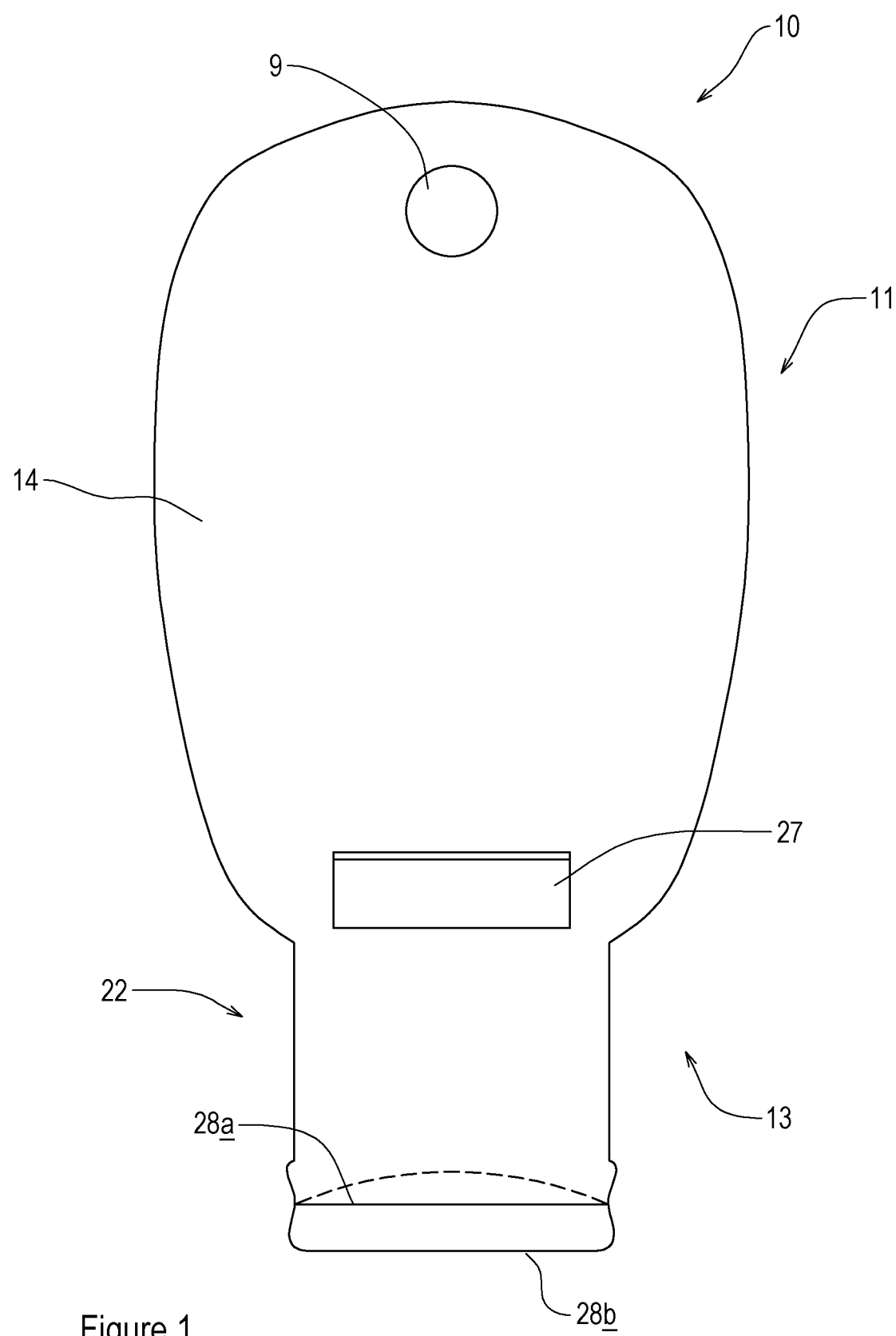
FIG. 1 is a front view of a first embodiment of an ostomy device in accordance with the invention with an outlet thereof shown in an unrolled condition.
Figure 2:
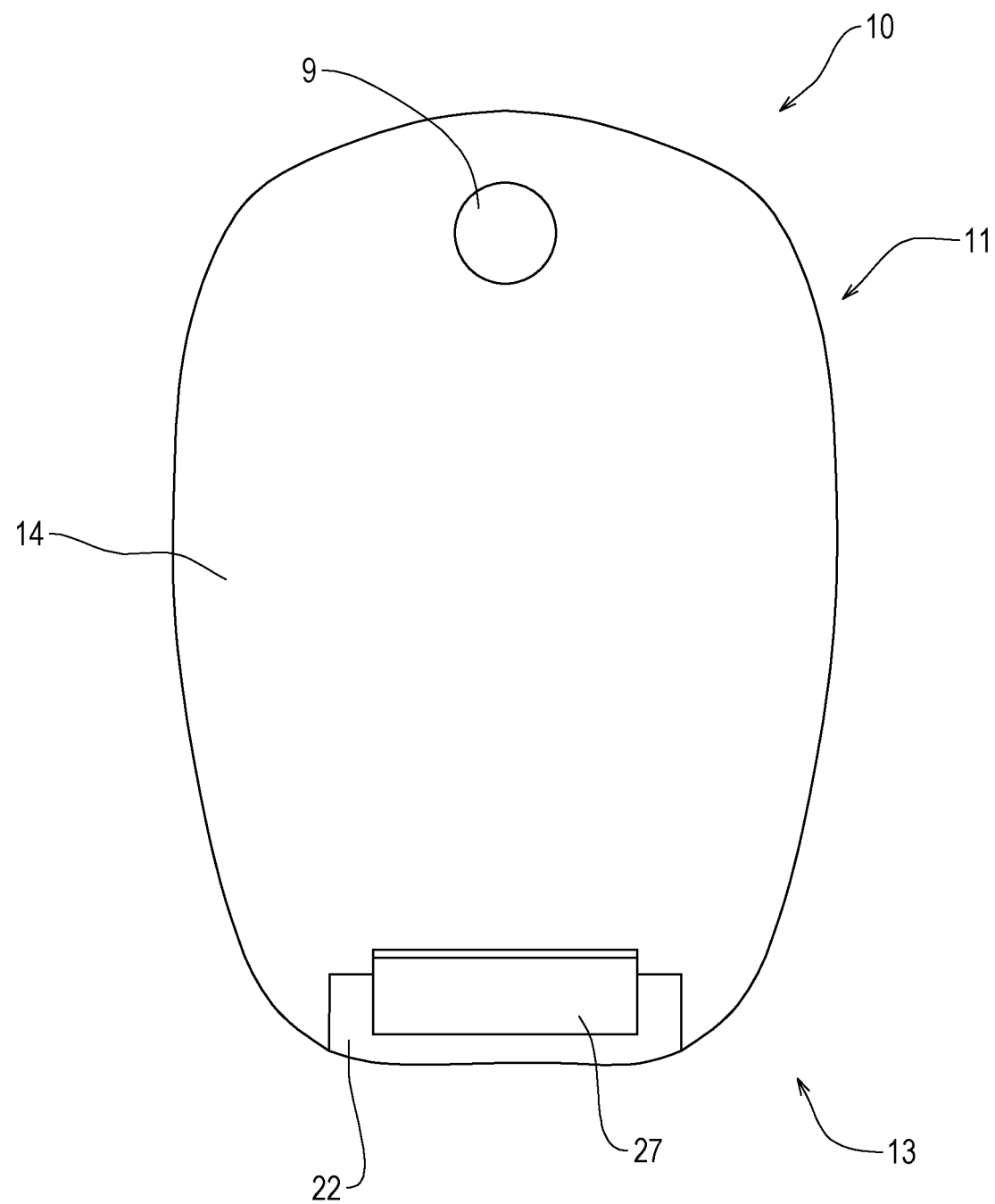
FIG. 2 is a front view of the device of FIG. 1 but with the outlet thereof shown in a rolled, i.e. closed, condition.

Referring to the figures, these show a first embodiment of an ostomy appliance in accordance with the present invention, shown generally at 10. The ostomy appliance 10 has a top, or upper end, 11 and a bottom, or lower end, 13. The ostomy appliance 10 has first and second walls 12, 14 connected to each other at or near their peripheries, by any suitable means known in the art. For example, they could be adhered to each other or heat welded.

The first wall 12 includes a stoma-receiving opening 16 and supports a connection member or flange 20 for attaching the appliance 10 to a user. In the embodiment shown, the connection member 20 is a hydrocolloid wafer for securing the appliance 10 to the skin of a user around their stoma. Alternatively, the connection member 20 may be for attaching the appliance 10 to a flange for attaching the appliance to a user (e.g. a two-piece appliance as it is known in the art).

Figure 5:
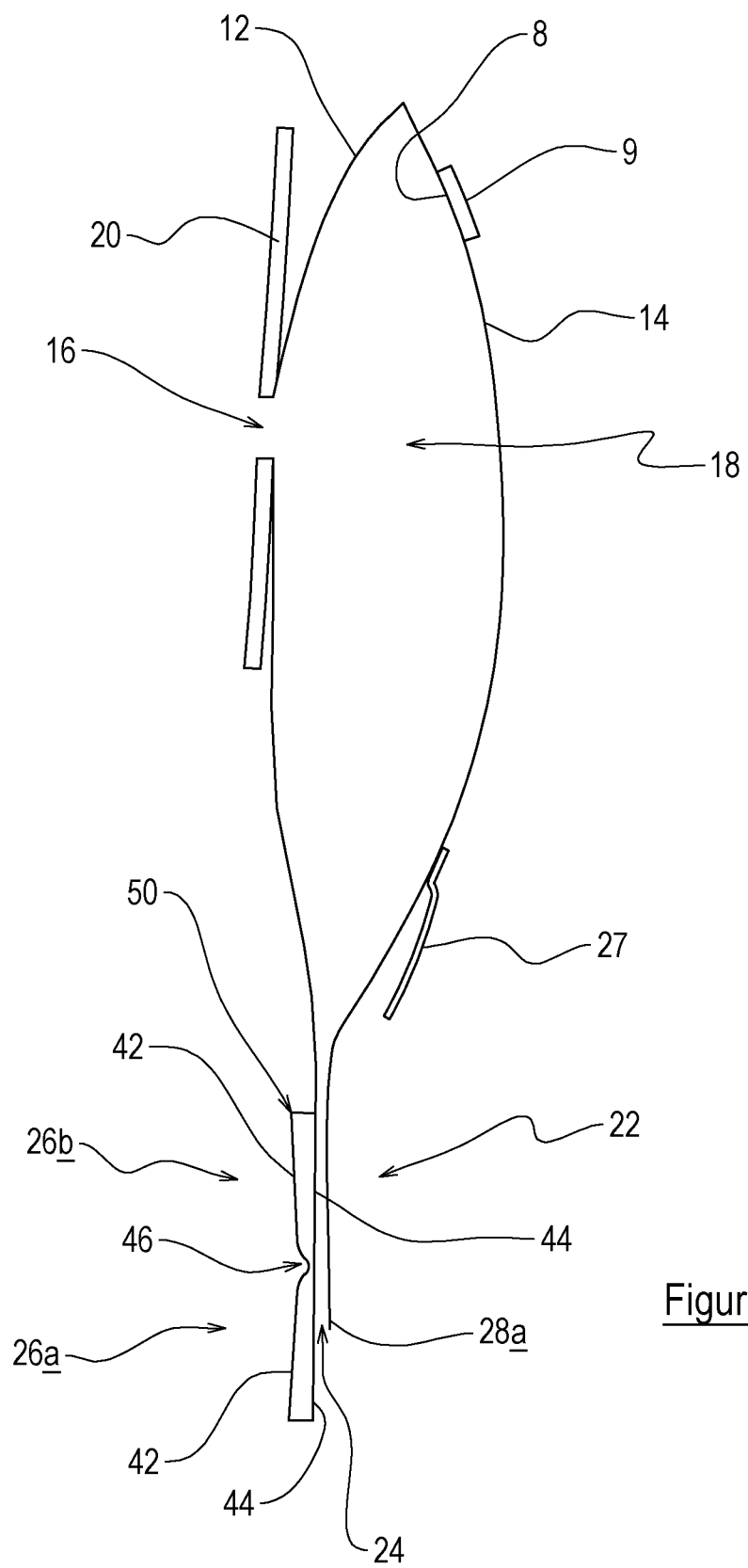
FIG. 5 is a side cross-sectional view of the ostomy device corresponding to FIG. 1.

Referring to FIG. 5, the first and second walls 12, 14 define a waste collecting cavity 18 therebetween. In some embodiments the first and/or second walls 12, 14 may be covered by comfort layers though these are not essential (which is not to suggest that other features are essential). The appliance 10 may also have a filter 9 positioned over a suitable gas vent 8 in either or both of the first 12 or second 14 walls.

The lower end 13 of the appliance 10 is provided with an outlet 22 formed by portions of the first and second walls 12, 14. The outlet 22 extends downwardly away from the stoma-receiving opening 16 and terminates at an opening 24. The opening 24 permits waste collected in the collecting cavity 18 to be expelled from the appliance 10.

In the present embodiment, first and second elongate stiffening members 26a, 26b are provided to assist with opening and closing of the opening 24. The stiffening members 26a, 26b each have a surface 44 which faces inwardly towards the outlet 22 and a surface 42 which faces outwardly towards a user. The inwardly 44 and outwardly 42 surfaces of the members 26a, 26b in this embodiment are generally flat, although they need not be. For example, they could be curved.

Figure 4:
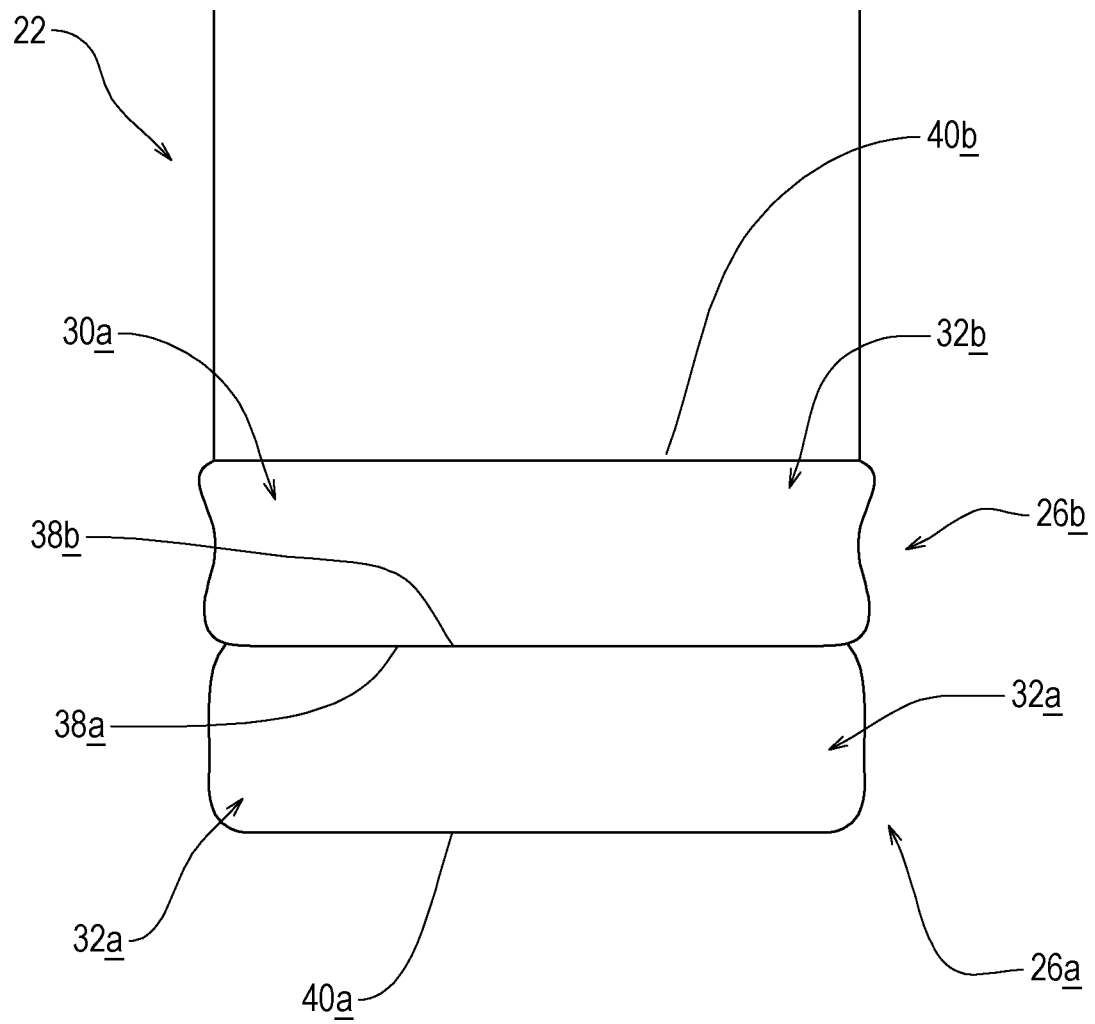
FIG. 4 is an enlarged rear view of the outlet of the device of FIG. 1.

When looking at the stiffening member 26b from FIG. 4 the member 26b has first and second lateral end portions 30b, 32b positioned at either side of the opening 24. First and second laterally extending edges or sides 38b, 40b extend across the outlet 22 between the first and second end portions 30b, 32b respectively. The first side 38b is positioned closer to the stoma-receiving opening than the second side 40b.

Figure 3:
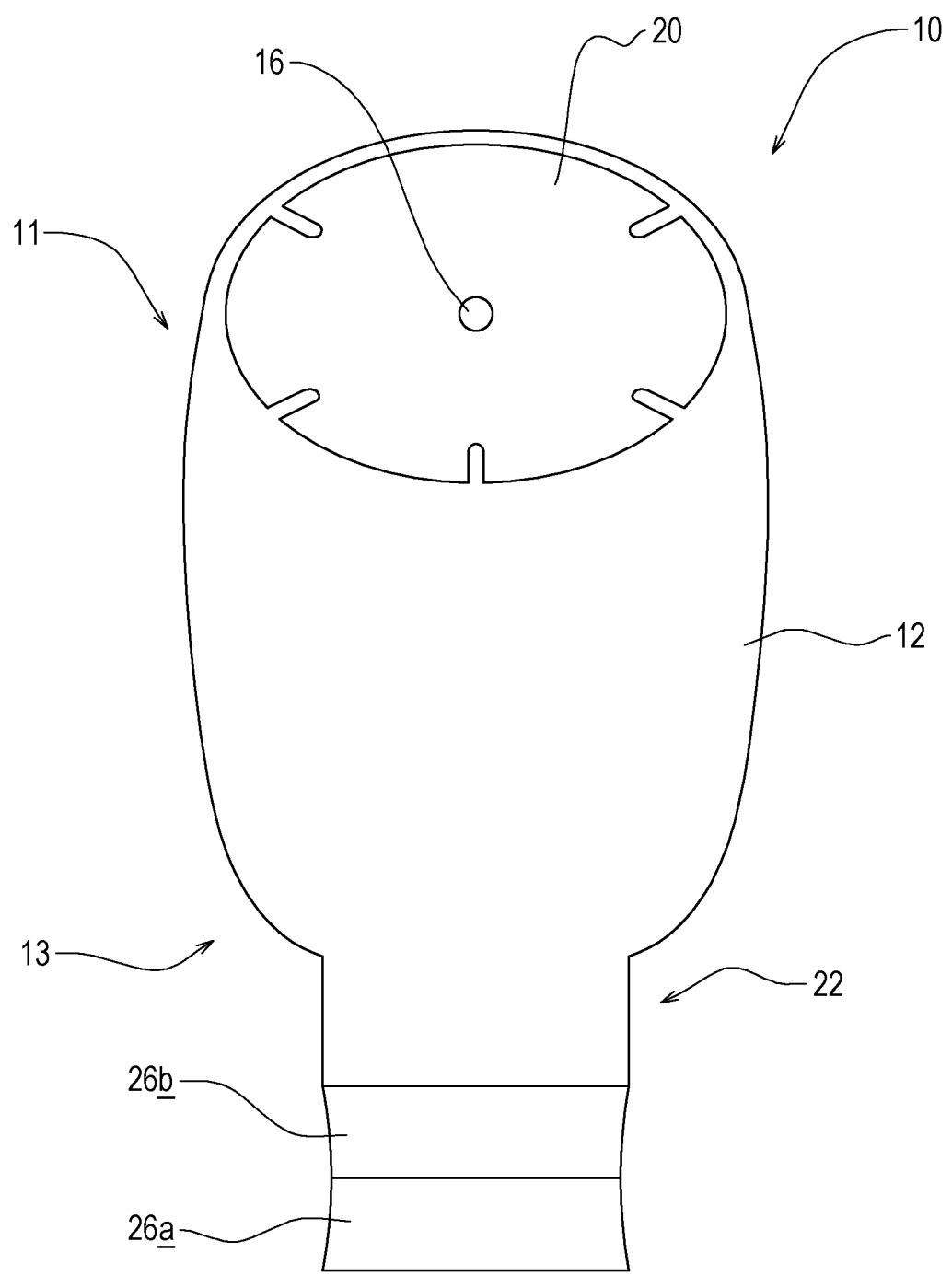
FIG. 3 is a rear view of the device of FIG. 1.

The first stiffening member 26a is connected, e.g. adhered or welded, to the exterior surface of the first wall 12, which faces the user and is positioned immediately adjacent the opening 24. The first stiffening member 26a extends laterally across the outlet 22 such that it extends generally perpendicularly to the direction in which waste exits the appliance 10, as shown in FIGS. 3 to 5. When looking at the stiffening member 26a from FIG. 4 the member 26a also has first and second lateral end portions 30a, 32a positioned at either side of the opening 24. First and second laterally extending edges or sides 38a, 40a extend across the outlet 22 between the first and second end portions 30a, 32a respectively. The second side 40a is positioned closer to the stoma-receiving opening than the first side 38a.

The second stiffening member 26b is positioned adjacent and above the first stiffening member 26a, further away from the opening 24 of the outlet 22 than the first stiffening member 26a, and is connected, e.g. adhered or welded, to the exterior surface of the first wall 12 (the same wall as the first stiffening member 26a). In particular, the first side 38b of the second stiffening member 26b abuts, or lies close to, the first side 38a of the first stiffening member 26a. The second stiffening member 26b also extends laterally across the outlet 22 such that it extends generally perpendicularly to the direction in which waste exits the appliance 10, as shown in FIGS. 3 to 5.

The stiffening member 26a tapers, or narrows, in thickness (when viewed in side cross-section) as it extends upwardly away from the opening 22 whilst the opposite is true for the stiffening member 26b. The stiffening member 26b also tapers, or narrows, in thickness (when viewed in side cross-section) as it extends downwardly towards the stiffening member 26a. As such, the inwardly 44 and outwardly 42 facing surfaces of each members 26a, 26b are inclined at an angle to each other.

In the present embodiment, the first stiffening member 26a is symmetrical to the second stiffening member 26b about a plane which extends between the stiffening members and which is generally perpendicular to a plane in which the first and/or second stiffening members 26a, 26b generally lie. In this embodiment the stiffening members 26a, 26b are substantially identical to each other.

Figure 6:
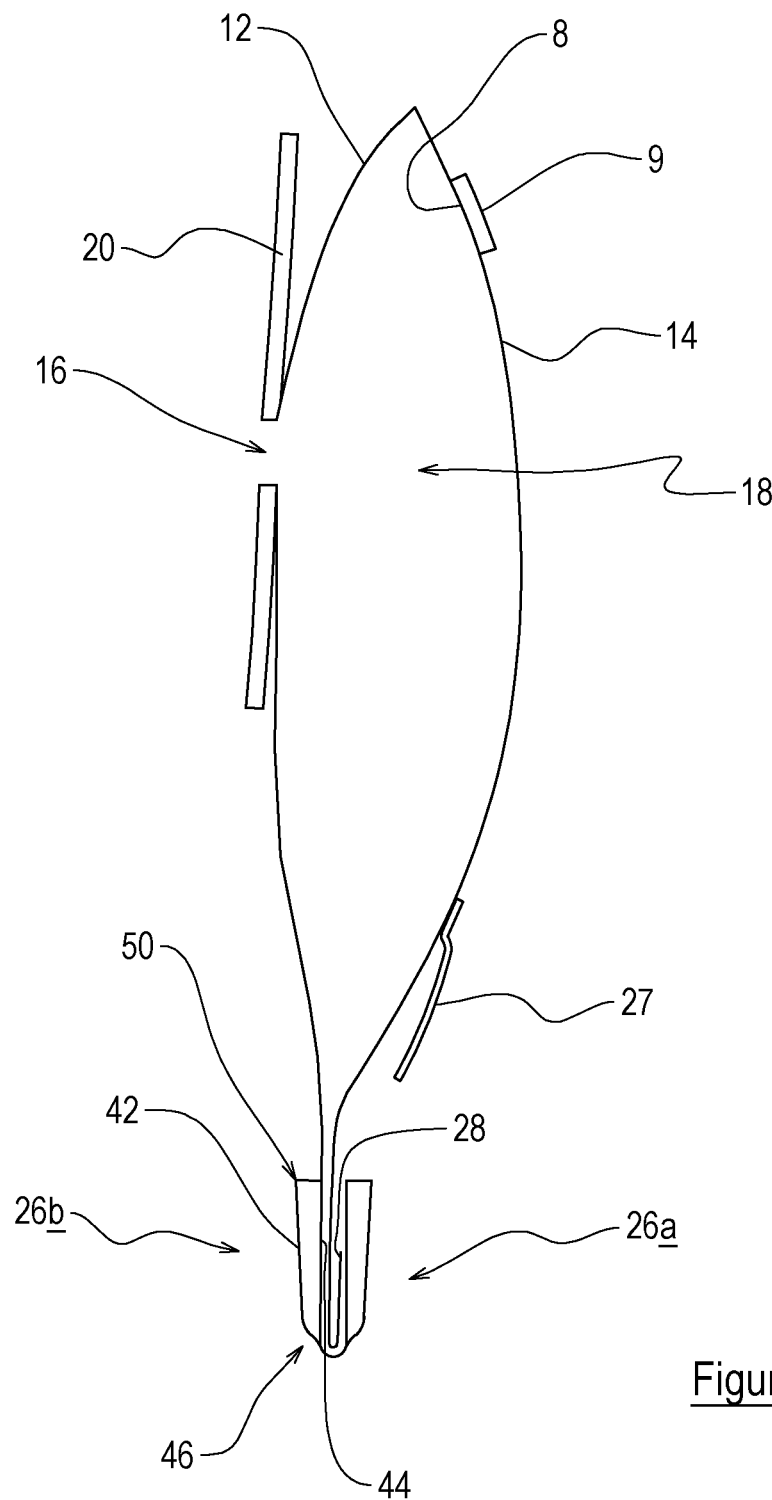
FIG. 6 is a side cross-sectional view of the ostomy device in a partially rolled up condition.
Figure 7:
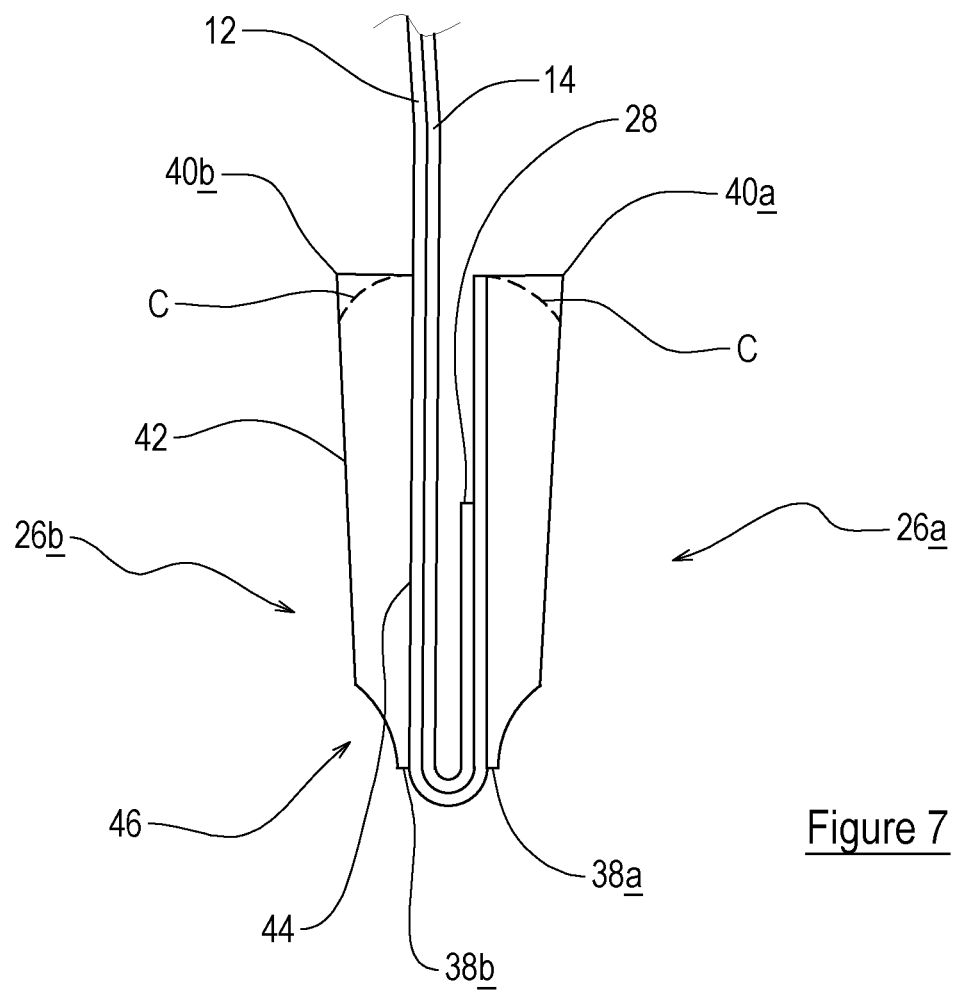
FIG. 7 is an enlarged cross-sectional view of the outlet section of FIG. 6.

When the member 26a is rotated 180 degrees upwardly and away from a user, it is then positioned on top of the other member 26b (see FIGS. 6 and 7). The inwardly facing surfaces of the members 26a, 26b then cooperate with each other so as to substantially close the outlet 22 therebetween.

The stiffening members 26a, 26b need only be stiff in the sense that they are relatively stiff compared to the walls 12, 14 of the ostomy appliance 10. In this embodiment the stiffening member 26a, 26b are injection moulded from a plastics material, but they could be made in other ways.

The outlet 22 may be stored, or stowed, by being rolled up around the stiffening members 26a, 26b, as is generally known in the art, and as shown in FIGS. 2 and 5 to 8. Such rolling up uses the laterally extending edges 38a, 38b, 40a, 40b of the members 26a, 26b as a fulcrum(s) to assist in tight closing of the outlet 24, to prevent leaking. In the present embodiment, the stiffening members 26a, 26b are rolled up two or three times, to seal the opening 24 in a closed condition. A flap 27 may be provided to secure the rolled up outlet 22 in its stowed condition. Any suitable fastening means, e.g. hook, and loop (Velcro) or adhesive, may be provided on respective faces of the flap 27 and outlet 22 to secure the outlet 22.

As briefly mentioned above, a thickness of the stiffening member 26b varies as it extends from the first side or edge 38b to the second side or edge 40b. In the present embodiment the cross-sectional shape, e.g. profile, of each stiffening member 26a, 26b is substantially constant as it extends across the outlet 22, though this need not be the case.

Referring to FIG. 5, the outlet 22 is formed from extensions or continuations of the first and second walls 12, 14 which terminate at respective wall edge 28a (for the wall 14) and 28b (for the wall 12). The wall edge 28a is spaced from the wall edge 28b, meaning that the wall edge 28a is positioned closer to the stoma receiving opening 16. Each wall edge 28a, 28b extends laterally across the outlet 22. In alternative embodiments the outlet 22 may be formed from only one continuous wall. Indeed, the outlet 22 may be formed separately from the remainder of the ostomy appliance 10 and welded or adhered to the remainder of the appliance 10 when it is manufactured. Preferably, no stiffening members are provided on the second wall 14 of the outlet 22. Therefore, the wall edge 28, or at least a portion of the wall edge 28, partially defines the opening 24 together with the lowermost edge 40 of the stiffening member 26a.

Whilst the wall edge 28a is relatively linear, embodiments are envisaged where the wall edge has a curved, e.g. convex or concave, portion (see broken lines in FIG. 1).

Referring to FIG. 7, a portion 46 of the surface 42 of the stiffening member 26b adjacent the edge 38b is concave. Whilst in this embodiment the edge 40b of the stiffening member 26b is angled, it could be convex, as denoted by the dashed line C in FIGS. 7 and 8. The same features are present in the corresponding portions of the stiffening member 26a.

Figure 8:
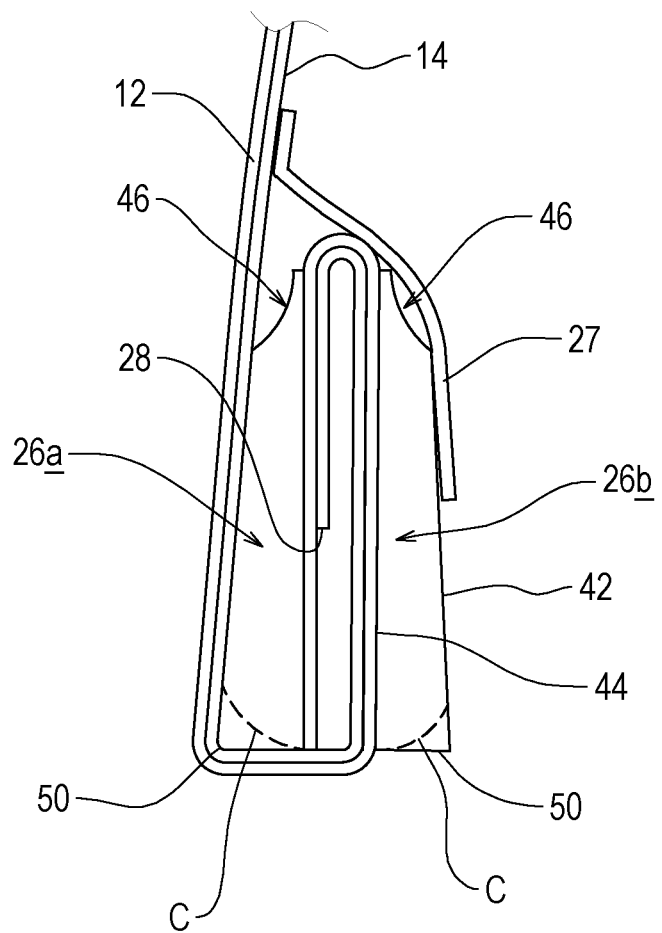
FIG. 8 is an enlarged cross-sectional view of the outlet section of FIG. 6 in a rolled up condition.

To open the opening 24 of the appliance 10 the stiffening members 26a, 26b are bent by applying finger pressure to their first and second respective end portions 30, 32, such that they bow to cause the walls of the outlet to bow away from each other. The opening 24 can then move to a closed condition due to the stiffening members 26 being biased to a relatively flat position when no finger pressure is applied to their lateral edges. The stiffening members 26a, 26b are then rolled up as shown in FIG. 8 and held in place by the flap 27.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The terms "near," "close to," "substantially," "generally," and the like are to be read as they would be by one of ordinary skill in the art at the time of invention in view of the present disclosure. Where it is determined that the disclosure does not provided enough certainty to one of skill in the art to ascertain the meaning of these terms, the permitted range of features modified by these terms are to be read with reference to industry norms in the field of use, and where such ranges are not defined, with reference to industry norms in the field of manufacturing of the designated feature.

What is claimed is:

1. A drainable ostomy appliance including:
   first and second walls connected to each other at or near their peripheries, the first wall having a stoma-receiving opening;
   a collecting cavity defined between the first and second walls;
   a connection member connected to the first wall for attaching the appliance to a user or for attaching the appliance to a flange for attaching the appliance to the user;
   an outlet which extends away from the stoma-receiving opening, the outlet terminating at an opening;

a first stiffening member positioned immediately adjacent the opening on a wall of the outlet that, when in use, faces the user, the first stiffening member extending across the outlet; and a second stiffening member positioned next to the first stiffening member, further away from the outlet than the first stiffening member and on the same wall as the first stiffening member, the second stiffening member also extending across the outlet, wherein the first and second stiffening members have first and second sides which extend across the outlet and the first side is positioned closer to the stoma-receiving opening than the second side;

wherein at least a portion of the thickness of the second stiffening member increases as it extends from the second side towards the first side.

2. The drainable ostomy appliance of claim 1, wherein the second side of the second stiffening member abuts or lies close to the first side of the first stiffening member.

3. The drainable ostomy appliance of claim 1, wherein at least a portion of the thickness of the second stiffening member increases linearly as it extends from the second side towards the first side.

4. The drainable ostomy appliance of claim 1, wherein a portion of the second stiffening member has a thickness that increases in a direction from the second side to the first side.

5. The drainable ostomy appliance of claim 1, wherein the thickness of the second stiffening member tapers as it extends from the first side towards the second side.

6. The drainable ostomy appliance of claim 1, wherein a thickness of the second stiffening member increases as it extends from the first side towards the second side.

7. The drainable ostomy appliance of claim 5, wherein at least a portion of the thickness of the second stiffening member increases linearly as it extends from the first side towards the second side.

8. The drainable ostomy appliance of claim 1, wherein the thickness of the second stiffening member at or near the first side of the second stiffening member is greater than the thickness of the second stiffening member at or near the second side of the second stiffening member.

9. The drainable ostomy appliance of claim 1, wherein the thickness of the second stiffening member at or near the first side of the second stiffening member is less than the thickness of the second stiffening member at or near the second side of the second stiffening member.

10. The drainable ostomy appliance of claim 1, wherein an outwardly facing surface of the second stiffening member, which surface faces away from the outlet, is substantially planar.

11. The drainable ostomy appliance of claim 1, wherein a first portion of an outwardly facing surface of the second stiffening member is concave, wherein the concave portion is positioned at or near the first side of the second stiffening member.

12. The drainable ostomy appliance of claim 11, wherein a second portion of an outwardly facing surface of the second stiffening member is concave, wherein the second concave portion is positioned at or near the second side of the second stiffening member.

13. The drainable ostomy appliance of claim 1, wherein a first portion of an outwardly facing surface of the second stiffening member is convex, wherein the convex portion is positioned at or near the second side of the second stiffening member.

14. The drainable ostomy appliance of claim 13, wherein a second portion of an outwardly facing surface of the second stiffening member is convex, wherein the second convex portion is positioned at or near the first side of the second stiffening member.

15. The drainable ostomy appliance of claim 1, wherein an inwardly facing surface of the second stiffening member, which surface faces towards the outlet, is substantially planar.

16. The drainable ostomy appliance of claim 1, wherein:

at least a portion of the thickness of the first stiffening member increases linearly as it extends from the second side towards the first side; and/or a portion of the first stiffening member has a thickness that increases in a direction from the second side to the first side; and/or the thickness of the first stiffening member tapers as it extends from the first side towards the second side; and/or a thickness of the first stiffening member increases as it extends from the first side towards the second side; and/or at least a portion of the thickness of the first stiffening member increases linearly as it extends from the first side towards the second side; and/or the thickness of the first stiffening member at or near the first side of the first stiffening member is greater than the thickness of the first stiffening member at or near the second side of the first stiffening member; and/or the thickness of the first stiffening member at or near the first side of the first stiffening member is less than the thickness of the first stiffening member at or near the second side of the first stiffening member; and/or an outwardly facing surface of the first stiffening member, which surface faces away from the outlet, is substantially planar; and/or a first portion of an outwardly facing surface of the first stiffening member is concave, wherein the concave portion is positioned at or near the first side of the first stiffening member; and/or a second portion of an outwardly facing surface of the first stiffening member is concave, wherein the second concave portion is positioned at or near the second side of the first stiffening member; and/or a first portion of an outwardly facing surface of the first stiffening member is convex, wherein the convex portion is positioned at or near the second side of the first stiffening member; and/or a second portion of an outwardly facing surface of the first stiffening member is convex, wherein the second convex portion is positioned at or near the first side of the first stiffening member; and/or an inwardly facing surface of the first stiffening member, which surface faces towards the outlet, is substantially planar.

17. The drainable ostomy appliance of claim 1, wherein the first stiffening member is symmetrical to the second stiffening member about a plane that extends generally perpendicular to a plane in which the first and/or second stiffening member(s) generally lie.

* * * * *